United States Patent [19]

Beestman

[11] Patent Number: 5,569,639
[45] Date of Patent: Oct. 29, 1996

[54] DRY FLOWABLE AGRICULTURAL COMPOSITIONS OF GLYPHOSATE AND SULFONYLUREA HERBICIDES MADE WITHOUT DRYING OF THE FINAL PRODUCT

[75] Inventor: George B. Beestman, Wilmington, Del.

[73] Assignee: E. I. Du Pont de Nemours and Company, Wilmington, Del.

[21] Appl. No.: 338,541

[22] PCT Filed: Jun. 10, 1993

[86] PCT No.: PCT/US93/05370

§ 371 Date: Dec. 9, 1994

§ 102(e) Date: Dec. 9, 1994

[87] PCT Pub. No.: WO93/25081

PCT Pub. Date: Dec. 23, 1993

[51] Int. Cl.[6] .......................... A01N 57/04; A01N 25/14
[52] U.S. Cl. ........................ 504/128; 71/DIG. 1
[58] Field of Search ................. 504/128, 127, 504/206, 211, 212, 213, 214, 215

[56] References Cited

U.S. PATENT DOCUMENTS

| 4,913,722 | 4/1990 | Felix et al. ................. 71/90 |
| 4,931,080 | 6/1990 | Chan et al. ................. 71/87 |
| 5,089,045 | 2/1992 | Bush et al. ................. 71/92 |
| 5,372,989 | 12/1994 | Geigle et al. ............ 504/116 |

FOREIGN PATENT DOCUMENTS

| 0206537 | 12/1986 | European Pat. Off. . |
| 0394211 | 10/1990 | European Pat. Off. . |
| WO90/07275 | 7/1990 | WIPO . |
| 0448538 | 9/1991 | WIPO . |
| WO91/13546 | 9/1991 | WIPO . |
| WO92/08353 | 5/1992 | WIPO . |

*Primary Examiner*—S. Mark Clardy

[57] ABSTRACT

A dry flowable agricultural composition made by mixing glyphosate and an anhydrous base salt with a sulfonylurea herbicide and stabilizer (sodium metasilicate or sodium carbonate), all of which is combined a heat activated binder without using a drying step.

9 Claims, No Drawings

5,569,639

DRY FLOWABLE AGRICULTURAL COMPOSITIONS OF GLYPHOSATE AND SULFONYLUREA HERBICIDES MADE WITHOUT DRYING OF THE FINAL PRODUCT

This application has been filed under 35 U.S.C. 371 from the international application PCT/U.S.93/05370 (WO 93/25081).

The present invention comprises a dry flowable agricultural composition of N-(phosphonomethyl)glycine (defined hereinafter as glyphosate) with and without a sulfonylurea herbicide and processes for the preparation of the composition without a drying step.

WO91/13546 discloses the preparation of dry flowable agricultural compositions comprising an active ingredient, binder and chemical stabilizer. Among the active ingredients disclosed are various sulfonylureas and N-(phosphonomethyl)glycine (glyphosate) with a disclosure that one or more may be used.

While generally useful for granulation without drying, WO91/13546 would not be useful for processing wetcake glyphosate or wet glyphosate salt without treatment according to the present invention.

WO90/07275 describes the preparation of glyphosate compositions or glyphosate salt granule compositions containing liquid surfactants. The ability to utilize a co-herbicide in the compositions is disclosed, and several sulfonylurea herbicides, including metsulfuron methyl, are specifically named.

The processes of the prior art have the disadvantage of requiring a drying step at some stage of production of the formulations disclosed and because the final products contain environmentally-sensitive chemicals such as sulfonylureas and other potentially volatile components, large and expensive air-purification systems are necessary in drying operations to prevent untoward chemical release.

SUMMARY OF THE INVENTION

The compositions of the invention are dry flowable agricultural compositions comprising glyphosate or glyphosate salt with a sulfonylurea. The process of the invention produces a free flowing granular composition without a drying step by heating. The resulting granules can also be described as free flowing, non-caking, low attrition glyphosate compositions.

A process for the preparation of a dry flowable agriculturally suitable composition whose pH when measured by a 1% by weight aqueous solution of the composition is 4 or higher which comprises a process selected from process A and process B, said process A comprising (a) blending the following ingredients
   (1) 1–70% wet glyphosate or wet glyphosate salt,
   (2) 0.1–40% of an anhydrous base salt,
   (3) 0–10% of an anti-caking agent, and
   (4) 0–1% of an anti-foaming agent to form a mixture I,
(b) milling mixture I to form a powder,
(c) blending the powder with 5–30% of a heat activated binder,
(d) heating to 60°–70° C., and
(e) cooling to 50° C. or lower, and said process B comprising
(f) blending 0.1–40% of an anhydrous base salt with 1–70% wet glyphosate or wet glyphosate salt to form a blended mixture I,
(g) adding to the blended mixture under blending conditions the following ingredients
   (1) 0–10% of an anti-caking agent,
   (2) 0–1% of an anti-foaming agent,
   (3) 0–20% of a stabilizer,
   (4) 0–40% of a sulfonylurea herbicide to form blended mixture II,
(h) milling blended mixture II to form a powder,
(i) blending mixtures I and II with 5–30% of a heat activated binder,
(j) heating to 60°–70° C., and
(k) cooling to 50° C. or lower wherein all of the above percentages are by weight based on the composition provided when a sulfonylurea is present the stabilizer is 0.1–20%.

The process of the invention is more advantageous when the glyphosate is a wetcake. Most preferably, the process of the invention is by process B. However, the process of the invention can also be carried out with glyphosate that has been previously dried because even when using dry glyphosate the resulting composition using some prior art methods would require drying. The processes of the invention do not require drying of the composition made from dry or from wet glyphosate. Preferably, the process of the invention is carried out with the presence of a sulfonylurea herbicide and stabilizer, but it also can be carried out without a sulfonylurea herbicide and without a stabilizer.

Another embodiment of the invention is a free flowing, non-caking, low attrition agriculturally suitable glyphosate composition comprising in weight percent based on the total composition weight (1) 1–70% previously dried or wetcake glyphosate or a wet glyphosate salt,
(2) 0–15% water,
(3) 0.1–40% anhydrous base salt,
(4) 0–10% anti-caking agent,
(5) 0–1% anti-foaming agent,
(6) 0.1–20% stabilizer,
(7) 5–30% heat activated binder, and
(8) 0.1–40% sulfonylurea herbicide provided that the pH of a 1% aqueous solution of the composition is higher than or equal to 4.

A preferred composition comprises, in weight precent based on total formulation weight, the above composition comprising:

(1) 20–60% of the glyphosate or glyphosate salt,
(2) 2–8% water,
(3) 4–30% anhydrous base salt,
(4) 0–5% anti-caking agent,
(5) 0–1% anti-foaming agent,
(6) 2–15% stabilizer,
(7) 10–25% heat-activated binder, and
(8) 0.5–20% sulfonylurea herbicide provided that the pH of a 1% aqueous solution of final product is greater than or equal to 4.

Anhydrous base salts in the compositions may convert free water to crystalline waters of hydration.

When a glyphosate salt is used, the preferred cation is sodium.

A preferred composition is that in which the base salt is an anhydrous sodium salt.

In addition, a preferred composition comprises a stabilizer which is sodium metasilicate.

A preferred binder is one selected from the class consisting of ethylene oxide/propylene oxide copolymer, polyethoxylated dinonylphenol, polyethylene glycol and mixtures of the foregoing.

Both glyphosate and the sulfonylureas hereinafter described are known herbicides.

What is meant by glyphosate is N-(phosphonomethyl)glycine of the structural formula

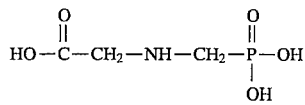

The preferred sulfonylurea herbicides are methyl 2-[[[[(4-methoxy-6-methyl-1,3,5-triazin-2-yl)amino]-carbonyl]amino]sulfonyl]benzoate (metsulfuron methyl) and methyl 2-[[[[(4,6-dimethyl-2-pyrimidinyl)amino]-carbonyl]amino]sulfonyl]benzoate.

DETAILED DESCRIPTION OF THE INVENTION

Conventional methods for preparing products containing glyphosate herbicide involve drying steps to remove water with heat at one or more stages of production. "Wetcake" glyphosate, so named because it can contain 2–20% water (typically 7–12% water) is obtained after processing of technical glyphosate acid. Prior to this invention, no granules of glyphosate prepared from "wetcake" glyphosate without a drying step were:

1) stable to chemically sensitive mixing partners such as sulfonylurea herbicides in the compositions,
2) non-caking and non-dusty, and
3) rapidly dissolving in water.

In the prior art, even sulfonylurea/glyphosate compositions prepared from dry glyphosate have required drying of the final product. Now according to the present invention drying for either situation is not necessary.

The instant invention comprises a novel composition and a novel process for preparing dry flowable compositions of glyphosate which do not require drying steps at any stage in the preparation. What is meant by drying is subjecting to heat or other means for the purpose of removing water. The sulfonylureas in the novel compositions of this invention do not decompose in the presence of the water because the water is believed to exist as crystalline water of hydration of the base salt, and thus is inocuous. The compositions of the instant invention are also free-flowing, non-caking, low attrition granules. Prior art granules made without a drying step are soft compositions without a stable structure.

The process of the instant invention is advantageous over known processes that require a drying step because fine particles or dust of environmentally-sensitive pesticides and other potentially volatile components may be released to the environment in the drying step. Known process conditions include large, expensive air-purification systems which are required to clean the large volumes of forced air required in drying operations at manufacturing facilities. The present invention precludes the need of such equipment.

Various salts are known to effect glyphosate activity and are routinely added to enhance weed control (e.g., see Nalewaja and Matysiak in *Weed Science*, 1991, 39, 622). Another advantage of the present invention is that the base salts known to enhance biological efficacy are already present and therefore need not be tank-mixed at the time of application.

A third advantage is that the binder present in the compositions of the present invention enhances the activity of the glyphosate. Normally, surfactants are tank-mixed with glyphosate to obtain a comparable improvement in efficacy and their use in tank-mixing is not necessary for the present compositions.

The nature of the glyphosate herbicide incorporated into the compositions can be acid "wetcake", dry acid, or a wet salt of the acid. When "wetcake" glyphosate, dry glyphosate or wet salt is used, an anhydrous base salt is added to make the glyphosate acid or salt composition of the invention which is a 1) dry, free-flowing and millable to a fine powder,
2) inert to decomposition of a sulfonylurea mixed with the glyphosate in the composition, and
3) available for direct processing to finished granules without a drying step.

For example, the granular composition of the invention prepared by the method exemplified in Example 1 below 1) show no change in metsulfuron methyl content after one week at 54° C.,
2) dissolve in water in less than two minutes as measured in the Break-up test,
3) have less than 5% attrition, and
4) are non-caking, as determined by the Collaborative International Pesticide Analytical Council (CIPAC) test.

The stabilizer is not required in the process of the invention when glyphosate or its salt is the only active ingredient. However, when dry glyphosate acid, wetcake glyphosate acid, or wet glyphosate salt are used in mixtures with sulfonylureas, then the weight percent of the stabilizer is greater than zero. Even "dry" glyphosate forms when mixed with the various components of processes of the prior art require drying. However, the compositions of this invention and the process of the invention do not require any drying step whether the starting glyphosate is wet or dry or whether a sulfonylurea is present or absent.

Useful anhydrous base salts are those which have hydrated forms with melting points above 60° C. Useful anhydrous base salts have cations that include ammonium, lithium, potassium, sodium, and polyvalent cations as that part of the salt with carbonate, carbonate/phosphate blends, citrate, metaborate, metasilicate, pyrophosphate, sulfate and tetraborate, as well as others. Ammonium salts are less desirable because of the problem of evolving ammonia. Potassium salts are less desirable because of the problem of forming hygroscopic compositions. Lithium salts are useful but can be more expensive than the corresponding sodium salt. Polyvalent cationic salts are useful but can deactivate glyphosate. Therefore, sodium base salts are preferred.

The use of anhydrous base salts that have hydrated forms with melting points less than 60° C. are ineffective in the compositions of the present invention with "wetcake". The sulfonylurea in the composition decomposes to such an extent that ineffective herbicidal formulations result. Anhydrous disodium phosphate has a hydrated form with a melting point below 60° C. When disodium phosphate was used instead of sodium pyrophosphate in Example 1 below, the components formed a solid mass which was inoperable as an agricultural formulation. However, disodium phosphate is effective in compositions with dry glyphosate acid as illustrated in Example 13 below.

Useful examples of anti-caking and anti-foaming agents are 10X sugar, Soap L®(i.e., sodium stearate) and other materials well-known to those in the art.

Suitable stabilizers comprise metal carbonate salts, metal acetate salts, or metal metasilicate salts which protect the sulfonylurea from decomposition in the formulation. The metal salts comprise divalent and monovalent metals.

Metal carbonate or metal metasilicate salts are used when glyphosate wetcake or wet glyphosate salt is used. Sodium carbonate or sodium metasilicate are preferred. When Example 1 below was repeated without sodium carbonate as the stabilizer, a 33% decomposition of metsulfuron methyl was observed after 1 week at 54° C. Similarly, when sodium acetate was used instead of sodium carbonate, 30% decomposition of the sulfonylurea was observed. When Example 12 was repeated without sodium carbonate as the stabilizer utilizing additional anhydrous base salt there was a 30% loss of metsulfuron methyl after two weeks at 54° C.

In addition to metal carbonates and metal metasilicates, metal acetate salts, preferably sodium acetate, may be used as stabilizers when dry glyphosate acid is used. As indicated in Example 14 hereinafter, when sodium acetate was used instead of sodium pyrophosphate (the anhydrous base) and sodium carbonate, <5% decomposition of metsulfuron methyl was observed after two weeks at 54° C.

The term "heat-activated binder" refers to any surface active material comprised of one or more components which dissolve rapidly in water, have sufficient viscosity near the melting point for tackiness, and are thus capable of acting as a binder when heat is applied. At some elevated temperature, the binder softens and melts, thereby becoming sticky enough to bind the pesticidal particles into granules. A preferred amount of binder used in this invention is 10–25% by weight based on the total weight of the composition. Suitable heat-activated binders include any component or mixture of components meeting the five criteria listed below. The binder must:

(1) have a melting point range within 40°–120° C., and preferably 45°–100° C.;
(2) have a hydrophile/lipophile balance (HLB) of about 14 or greater;
(3) dissolve in mildly-agitated water in 60 min. or less, preferably 50 min. or less;
(4) have a melt viscosity of at least 200 centipoise (cps); preferably 1000 cps or greater, and most preferred 2000 cps or greater; and
(5) have a difference of 5° C., and preferably 3° C. or less between the softening point and onset of solidification.

Examples of suitable heat-activated binders, which are not intended to be limiting, are ethylene oxide/propylene oxide copolymers such as Pluronic® F108, polyethoxylated dinonylphenol such as Macol® DNP150, polyethylene glycols such as PEG 8000.

A "sulfonylurea herbicide" can be any one of the entire class of herbicides containing the following structural moiety, and any closely related chemical functionalities.

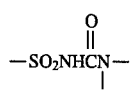

Preferred are compositions wherein the sulfonylurea herbicide is a compound of the formula

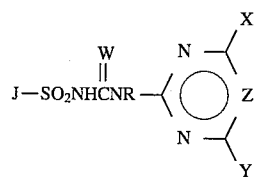

wherein:

J is

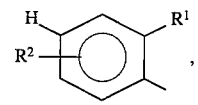   J-1

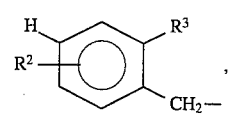   J-2

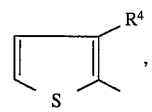   J-3

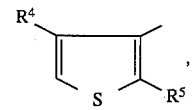   J-4

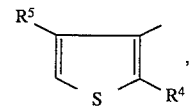   J-5

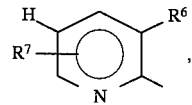   J-6

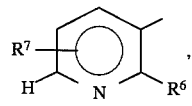   J-7

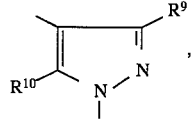   J-8

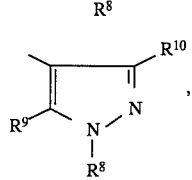   J-9

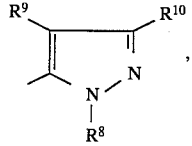   J-10

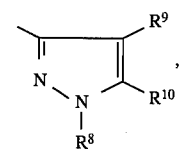   J-11

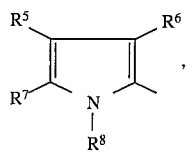 J-12

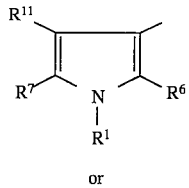 J-13 or

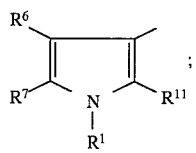 J-14 ;

R is H or CH$_3$;

R$^1$ is F, Cl, Br, NO$_2$, C$_1$–C$_4$ alkyl, C$_1$–C$_4$ haloalkyl, C$_3$–C$_4$ cycloalkyl, C$_2$–C$_4$ haloalkenyl, C$_1$–C$_4$ alkoxy, C$_1$–C$_4$ haloalkoxy, C$_2$–C$_4$ alkoxyalkoxy, CO$_2$R$^{12}$, C(O)NR$^{13}$R$^{14}$, SO$_2$NR$^{15}$R$^{16}$, S(O)$_n$R$^{17}$, C(O)R$^{18}$, CH$_2$CN or L;

R$^2$ is H, F, Cl, Br, CN, CH$_3$, OCH$_3$, SCH$_3$, CF$_3$ or OCF$_2$H;

R$^3$ is Cl, NO$_2$, CO$_2$CH$_3$, CO$_2$CH$_2$CH$_3$, SO$_2$N(CH$_3$)$_2$, SO$_2$CH$_3$, SO$_2$CH$_2$CH$_3$, OCH$_3$, or OCH$_2$CH$_3$; R$^4$ is C$_1$–C$_3$ alkyl, C$_1$–C$_2$ haloalkyl, C$_1$–C$_2$ alkoxy, C$_2$–C$_4$ haloalkenyl F, Cl, Br, NO$_2$, CO$_2$R$^{12}$, C(O)NR$^{13}$R$^{14}$, SO$_2$NR$^{15}$R$^{16}$, S(O)$_n$R$^{17}$, C(O)R$^{18}$ or L;

R$^5$ is H, F, Cl, Br or CH$_3$;

R$^6$ is C$_1$–C$_3$ alkyl, C$_1$–C$_2$ alkoxy, C$_2$–C$_4$ haloalkenyl, F, Cl, Br, CO$_2$R$^{12}$, C(O) NR$^{13}$R$^{14}$, SO$_2$NR$^{15}$R$^{16}$, S(O)$_n$R$^{17}$, C(O) R$^{18}$ or L;

R$^7$ is H, F, Cl, CH$_3$ or CF$_3$;

R$^8$ is H, C$_1$–C$_3$ alkyl or pyridyl;

R$^9$ is C$_1$–C$_3$ alkyl, C$_1$–C$_2$ alkoxy, F, Cl, Br, NO$_2$, CO$_2$R$^{12}$, SO$_2$NR$^{15}$R$^{16}$, S(O)$_n$R$^{17}$, OCF$_2$H, C(O)R$^{18}$, C$_2$–C$_4$ haloalkenyl or L;

R$^{10}$ is H, Cl, F, Br, C$_1$–C$_3$ alkyl or C$_1$–C$_2$ alkoxy;

R$^{11}$ is H, C$_1$–C$_3$ alkyl, C$_1$–C$_2$ alkoxy, C$_2$–C$_4$ haloalkenyl, F, Cl, Br, CO$_2$R$^{12}$, C(O)NR$^{13}$R$^{14}$, SO$_2$NR$^{15}$R$^{16}$, S(O)$_n$R$^{17}$, C(O)R$^{18}$ or L;

R$^{12}$ is C$_1$–C$_3$ alkyl optionally substituted by halogen, C$_1$–C$_2$ alkoxy or CN, allyl or propargyl;

R$^{13}$ is H, C$_1$–C$_3$ alkyl or C$_1$–C$_2$ alkoxy;

R$^{14}$ is C$_1$–C$_2$ alkyl;

R$^{15}$ is H, C$_1$–C$_3$ alkyl, C$_1$–C$_2$ alkoxy, allyl or cyclopropyl;

R$^{16}$ is H or C$_1$–C$_3$ alkyl;

R$^{17}$ is C$_1$–C$_3$ alkyl, C$_1$–C$_3$ haloalkyl, allyl or propargyl;

R$^{18}$ is C$_1$–C$_4$ alkyl, C$_1$–C$_4$ haloalkyl or C$_3$–C$_5$ cycloalkyl optionally substituted by halogen;

n is 0, 1 or 2;

L is

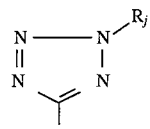

R$_j$ is H or C$_1$–C$_3$ alkyl;

W is O or S;

X is H, C$_1$–C$_4$ alkyl, C$_1$–C$_4$ alkoxy, C$_1$–C$_4$ haloalkoxy, C$_1$–C$_4$ haloalkyl, C$_1$–C$_4$ haloalkylthio, C$_1$–C$_4$ alkylthio, halogen, C$_2$–C$_5$ alkoxyalkyl, C$_2$–C$_5$ alkoxyalkoxy, amino, C$_1$–C$_3$ alkylamino or di (C$_1$–C$_3$ alkyl) amino;

Y is H, C$_1$–C$_4$ alkyl, C$_1$–C$_4$ alkoxy, C$_1$–C$_4$ haloalkoxy, C$_1$–C$_4$ alkylthio, C$_1$–C$_4$ haloalkylthio, C$_2$–C$_5$ alkoxyalkyl, C$_2$–C$_5$ alkoxyalkoxy, amino, C$_1$–C$_3$ alkylamino, di(C$_1$–C$_3$ alkyl )amino, C$_3$–C$_4$alkenyloxy, C$_3$–C$_4$ alkynyloxy, C$_2$–C$_5$ alkylthioalkyl, C$_2$–C$_5$ alkylsulfinylalkyl, C$_2$–C$_5$ alkylsulfonylalkyl, C$_1$–C$_4$ haloalkyl, C$_2$–C$_4$ alkynyl, C$_3$–C$_5$ cycloalkyl, azido or cyano;

z is CH or N;

and their agriculturally suitable salts;

provided that:

(a) when X and/or Y is C$_1$ haloalkoxy, then Z is CH;

(b) when X is halogen, then Z is CH and Y is OCH$_3$, OCH$_2$CH$_3$, N(OCH$_3$)CH$_3$, NHCH$_3$, N(CH$_3$)$_2$ or OCF$_2$H.

Even more preferred are compositions wherein the sulfonylurea is selected from the group:

2-chloro-N-[[(4-methoxy-6-methyl-1,3,5-triazin-2-yl)amino]carbonyl]benzenesulfonamide (chlorsulfuron);

methyl 2- [[[[(4,6-dimethyl-2-pyrimidinyl) amino]-carbonyl]amino]sulfonyl]benzoate (sulfometuron methyl);

ethyl 2-[[[[(4-chloro-6-methoxy-2-pyrimidinyl)-amino]carbonyl]amino]sulfonyl]benzoate (chlorimuron ethyl);

methyl 2-[[[[(4-methoxy-6-methyl-1,3, 5-triazin-2yl) amino]carbonyl]amino]sulfonyl]benzoate (metsulfuron methyl);

methyl 2-[[[[(4,6-dimethoxy-2-pyrimidinyl) amino]carbonyl ]amino]sulfonyl]-6-(trifluoromethyl) -3-pyridinecarboxylate;

methyl 2- [[[[[4-ethoxy-6- (methylamino) -1,3,5- triazin-2-yl]amino]carbonyl]amino]sulfonyl]-benzoate;

2-(2-chloroethoxy) -N- [[(4-methoxy-6-methyl-1,3,5-triazin-2-yl) amino]carbonyl]benzenesulfonamide (triasulfuron);

ethyl 5-[[[[(4,6-dimethoxy-2-pyrimidinyl)amino]-carbonyl]amino]sulfonyl]-1-methyl-1H-pyrazole-4-carboxylate;

N-[[(4,6-dimethoxy-2-pyrimidinylamino]carbonyl]-3-(ethylsulfonyl)-2-pyridinesulfonamide;

methyl 3-[[[[(4-methoxy-6-methyl-1,1,3,5-triazin-2-yl)amino]carbonyl]amino]sulfonyl]-2-thiophenecarboxylate;

methyl 2-[[[[N- (4-methoxy-6-methyl-1,3,5-triazin-2-yl)-N-methylamino]carbonyl]amino]sulfonyl]benzoate (tribenuron methyl); methyl 2-[[[[[(4,6-dimethoxy-2-pyrimidinyl)amino ]-carbonyl]amino]sulfonyl]methyl ]benzoate (bensulfuron methyl );

N- [[(4,6-dimethoxy-2-pyrimidinyl) -amino]carbonyl]-1-methyl-4 - (2-methyl-2H-tetrazol-5-yl ) - 1H-pyrazole-5-sulfonamide;

methyl 2-[[[[[4-(dimethylamino)-6- (2,2,2-trifluoroethoxy)- 1,3, 5-triazin-2-yl]amino]-carbonyl ]amino]sulfonyl ]-3-methylbenzoate;

2-[[[[(4,6-dimethoxy-2 -pyrimidinyl) amino]-carbonyl] amino]sulfonyl]-N, N-dimethyl-3-pyridinecarboxamide (nicosulfuron); and methyl 2-[[[[[4,6-bis(difluoromethoxy)-2-pyrimidinyl] amino]carbonyl]amino]sulfonyl]benzoate.

One skilled in the art can select dyes, humectants, spreading agents, corrosion inhibitors, fillers, stickers, odorants, bitterants or other formulation ingredients to obtain some special properties and still be within the scope of this invention.

A process for preparing the compositions is described in the instant invention. The process comprises first blending the glyphosate with an anhydrous base salt. All other components except the binder are then added and the mixture is milled to a powder. The powder is combined with a binder in a V-blender, and then tumbled and heated to about 60°–70° C. The granules are then cooled to about 50° C. or lower and collected.

The preferred process is that in which the glyphosate is in the form of a wetcake.

A particular preferred composition of the invention as described above includes a sulfonylurea selected from the group consisting of chlorsulfuron; sulfometuron methyl; chlorimuron ethyl; metsulfuron methyl; tribenuron methyl; bensulfuron methyl; nicosulfuron; triasulfuron; methyl 2-[[ [[(4,6-dimethoxy-2-pyrimidinyl) amino]carbonyl]amino] sulfonyl]-6-(trifluoromethyl)-3-pyridinecarboxylate; methyl 2-[[[[[4-ethoxy-6-(methylamino)-1,3,5-triazin-2-yl]-amino] carbonyl]amino]sulfonyl]benzoate; ethyl 5-[[[[(4,6-dimethoxy-2-pyrimidinyl)amino]carbonyl]amino]-sulfonyl] -1-methyl-1H-pyrazole-4-carboxylate; N-[[(4,6-dimethoxy-2-pyrimidinylamino]carbonyl]-3-(ethyl-sulfonyl)-2-pyridinesulfonamide; N-[[(4;6-dimethoxy-2-pyrimidinyl)amino]carbonyl]-1-methyl-4-(2-methyl-2H-tetrazol-5-yl)-1H-pyrazole-5-sulfonamide; and methyl 2-[[[ [[4-(dimethylamino)-6-(2,2,2-trifluoroethoxy)-1,3,5-triazin-2-yl]amino]carbonyl]amino]sulfonyl]-3-methylbenzoate.

The heating step in the process is not a drying step but an activation of the binder. No weight loss (e.g., through water loss) was observed when a blender containing wetcake glyphosate and the other ingredients of the compositions of this invention was weighed before and after heat activation. A drying step in a typical formulation process requires longer heating times, higher temperatures, and a forced air system to remove the water vapor and other volatiles. As indicated above, the forced air must be purified to prevent contamination of the environment, and these purification systems are large and expensive. No such purification systems are required in the heat activation step in the process of the present invention.

The fact that the final composition weight equals the sum of the weights of the components suggests that the anhydrous base salt converts free water from glyphosate wetcake to crystalline waters of hydration. Waters of hydration are not removed in the heat activated granulation step, do not decompose sulfonylureas, and do not facilitate reaction of glyphosate with the stabilizer. If free water were present and sodium carbonate was the stabilizer, glyphosate would react with the sodium carbonate to liberate carbon dioxide and the sulfonylurea would decompose. No weight loss occurred during heat activated granulation and the sulfonylureas remained stable. Therefore our hypothesis is that the base salt reacts with free water to form water of hydration.

In the Examples below, the abbreviation "a.e." is defined as acid equivalents. The abbreviation "rh" is defined as round hole. The percentages indicated are by weight.

Noncaking was measured by the CIPAC test which is described in MT 172 "Flowability of Water Dispersible Granules after Heat Test Under Pressure". The Attrition test measures the stability of the granules to break down under dry conditions. The granules of the present invention exhibit low attrition as determined by the Attrition test in U.S. Pat. No. 3,920,442. A sample of the granules to be tested are separated into size fractions first by sieving of granules passing a 10 mesh screen so the largest aggregate in any fraction has a diameter no more than 1.4 times larger than the smallest granule in the fraction. For example, in the fraction isolated between 10 and 14 mesh sieves, the largest aggregate has a diameter of approximately 2 mm and the smallest aggregate has a diameter slightly larger than 74 microns. Other suitable sieve fractions can be isolated, for example, between 25 and 35 mesh sieves, 30 and 40 mesh sieves, 100 and 140 mesh sieves, etc. A three gram sample from the isolated size fraction is placed in a 0.24 liter glass jar, 60 mm outer diameter by 54 mm inner diameter by 100 mm long, fitted with a screw cap. One hundred and twenty 0.64 cm diameter and fourteen 1.3 cm diameter steel balls are added to the jar, the jar is capped and is then placed in a rotating device such as a jar roller and rotated around its longitudinal axis at 25–26 RPM for exactly two minutes.

The jar is removed from the roller, its contents discharged carefully to prevent further grinding of the remaining aggregates onto a nest of U.S. Standard sieves, consisting of a No. 10 sieve to remove the balls and a sieve in which the sieve opening is equal to the diameter of the smallest aggregates in the original sample, and a pan. The stacked sieves are gently rotated to separate the steel balls from the sample. The No. 10 sieve is then removed and the screening of the sample on the other sieve continued with rotation and tapping, until all the fines are collected in the pan. The fine material in the pan is weighed, and the weight percent of mechanical breakdown of the aggregates is calculated:

$$\text{Attrition \%} = \frac{\text{weight of fines in grams} \times 100}{\text{sample weight in grams}}$$

Attrition values of less than 40%, and preferably less than 30%, are acceptable.

The Break-up test measures the time it takes for the granules to form a dispersion in water or dissolve in water. A 0.5 sample of granules is added to a 100 mL graduated cylinder (internal height after stoppering is 22.5 cm, inner diameter is 28 mm) containing 90 mL of distilled water at 25° C. and the cylinder clamped in the center, stoppered and rotated about the center at 8 RPM until the sample is completely broken up in the water. The time for break up is measured. The granules of the invention should break up in less than 5 minutes, preferably less than 3 minutes.

EXAMPLE 1

A mixture of 45.88 g of "wetcake" glyphosate (11% water, 86.3% a.e.) and 31.67 g of anhydrous sodium pyrophosphate as blended in a Black and Decker Handy Chopper® mill for 10 minutes, and hammer-milled through a 0.02 rh screen. All other components except the binder, i.e., 1.10 g of 10X sugar, 0.55 g of Soap L®, 1.16 g of metsulfuron methyl and 9.85 g of sodium carbonate, were hammer-milled through a 0.02 rh screen.

The milled glyphosate/base salt mixture and milled powders were blended together for 5 minutes, combined with 19.8 g of Pluronic® F108 (<40 mesh), an ethylene oxide/propylene oxide block polymer with 80% ethylene oxide and 20% propylene oxide units, in a V-blender, tumbled as the temperature of the powders were brought to 70° C. with a hair dryer, cooled to 50° C. and the granules collected.

They dissolved in water in less than 2 minutes as measured by the Break-up test. Less than 5% attrition was observed in the Attrition test, and the granules were non-caking (CIPAC test). The granules obtained showed no decomposition of the metsulfuron methyl after 1 week at 54° C.

Examples 2–6 indicate that different binders or binder mixtures can be used.

EXAMPLE 2

Example 1 was repeated using 45.88 g of glyphosate (11% water, 86.3% a.e.), 25.08 g of anhydrous sodium pyrophosphate, 1.10 g of 10X sugar, 0.55 g of Soap L®, 1.15 g of metsulfuron methyl (95%), 9.85 g of sodium carbonate and 26.40 g of Macol®DNP 150 (20/80 mesh), a polyethylated dinonylphenol with 150 ethylene oxide units made by Mazer Chemicals. The granules dissolved in 90 seconds.

EXAMPLE 3

Example 2 was repeated using PEG Carbowax® 8000 (20/80 mesh) instead of Macol® . DNP 150. The granules dissolved in 30 seconds.

EXAMPLE 4

Example 2 was repeated using Pluronic® F108/disodium phosphate 4/1 (20/80 mesh) instead of Macol® DNP 150. The mixture was prepared by melting and mixing the components together, grinding the solids with a laboratory mill and collecting the 20/80 mesh fraction. The granules dissolved in 285 seconds.

EXAMPLE 5

Example 2 was repeated using Pluronic® F108/Siponate® DS10 (4/1 mixture, 20/80 mesh) instead of Macol® DNP 150. The mixture was prepared by melting and mixing the components together, grinding the solids with a laboratory mill and collecting the 20/80 mesh fraction. The granules dissolved in 135 seconds.

EXAMPLE 6

Example 2 was repeated using Pluronic® F108 (20/80 mesh) instead of Macol® DNP 150. The granules dissolved in 255 seconds.

Examples 7–10 show that the binder size can be regulated to affect the rate at which the granules dissolve in water.

EXAMPLE 7

Example 2 was repeated using Pluronic® F108 (20/70 mesh) instead of 20/80 mesh. The granules dissolved in 280 seconds.

EXAMPLE 8

Example 2 was repeated using Pluronic® F108 (30/70 mesh) instead of 20/80 mesh. The granules dissolved in 190 seconds.

EXAMPLE 9

Example 2 was repeated using Pluronic® F108 (40/60 mesh) instead of 20/80 mesh. The granules dissolved in 135 seconds.

EXAMPLE 10

Example 2 was repeated using Pluronic® F108 (40/70 mesh) instead of 20/80 mesh. The granules dissolved in 120 seconds.

EXAMPLE 11

This Example shows that a portion of the anhydrous base salt can be replaced with additional metsulfuron methyl, and that additional ingredients may be added.

Example 1 was repeated using 45.88 g of glyphosate (11% water, 86.3% a.e.), 14.25 g of anhydrous sodium pyrophosphate, 1.10 g of 10 sugar, 0.55 g of Soap L® (sodium stearate), 11.00 g of Lomar® PW (a dispersing agent comprising a condensed naphthalene sulfonate), 1.10 g of Wessalon® 50S (a precipitated silica filler/carrier), 3.43 g of metsulfuron methyl (95%), 10.69 g of sodium carbonate and 22.00 g of Macol® DNP 150 (<20 mesh). The Lomar® PW and Wessalon® 50S were combined with the sugar, Soap L®, metsulfuron methyl and sodium carbonate.

The granules obtained showed no decomposition of the metsulfuron methyl after 1 week at 54° C. They were dispersed in water in less than 2 minutes by the Break-up test. Less than 5% attrition was observed in the Attrition test, and the granules were non-caking (CIPAC test).

Examples 12–15 illustrate that the dry acid form of glyphosate may be used to produce granules without drying of the final products. In these cases, anhydrous bases for which the hydrated forms melt below 60° C. may be added. Stabilizers are required.

EXAMPLE 12

A mixture of 40.82 g of glyphosate acid (97% a.e.), 34.53 g of sodium pyrophosphate, 1.10 g of 10X sugar and 0.55 g of Soap L® were blended in a Black and Decker Handy Chopper® mill for 10 minutes, and hammer-milled through a 0.02 rh screen. 1.16 g of metsulfuron methyl and 9.85 g of sodium carbonate were similarly blended for 10 minutes, and hammer-milled through a 0.02 rh screen. The two milled mixtures were combined and treated with 22.00 g of Pluronic® F108 (<20 mesh) in a V-blender, tumbled as the temperature of the powders were brought to 70° C. with a hair dryer, cooled to 50° C. and the granules collected.

A <5% loss of metsulfuron methyl was observed after 2 weeks at 54° C.

EXAMPLE 13

Example 12 was repeated using disodium phosphate instead of sodium pyrophosphate. A <5% loss of metsulfuron methyl was observed after 2 weeks at 54° C.

EXAMPLE 14

Example 12 was repeated using 44.38 g of sodium acetate instead of sodium pyrophosphate and sodium carbonate. A <5% loss of metsulfuron methyl was observed after 2 weeks at 54° C.

EXAMPLE 15

Example 12 was repeated using 44.38 g of sodium carbonate instead of sodium pyrophosphate. A <5% loss of metsulfuron methyl was observed after 2 weeks at 54° C.

EXAMPLE 16

A mixture of 46.48 g of "wetcake" glyphosate (11% water, 86.3% a.e.) and 32.08 g of anhydrous sodium pyrophosphate as blended in a Black and Decker Handy Chopper® mill for 10 minutes, and hammer-milled through a 0.02 rh screen. All other components except the binder, i.e., 1.11 g of 10×sugar, 0.56 g of Soap L® and 9.85 g of sodium carbonate, were hammer-milled through a 0.02 rh screen. The milled glyphosate/base salt mixture and milled powders were blended together for 5 minutes, combined with 19.8 g of Pluronic® F108 (<40 mesh), an ethylene oxide/propylene oxide block polymer with 80% ethylene oxide and 20% propylene oxide units, in a V-blender, tumbled as the temperature of the powders were brought to 70° C. with a hair dryer, cooled to 50° C. and the granules collected.

The granules dissolved in water in less than 2 minutes as measured by the Break-up test. Less than 5% attrition was observed in the Attrition test, and the granules were non-caking (CIPAC test).

EXAMPLE 17

Example 1 was repeated using 9.85 g of sodium metasilicate instead of sodium carbonate. The granules obtained showed no decomposition of the metsulfuron methyl after two weeks at 54° C.

EXAMPLE 18

Example 2 was repeated using 9.85 g of sodium metasilicate instead of sodium carbonate, and PEG Carbowax® 8000 (20/80 mesh) instead of Macol® DNP 150. The granules obtained showed no decomposition of the metsulfuron methyl after two weeks at 54° C.

What is claimed is:

1. A process for the preparation of a dry flowable agriculturally suitable composition whose pH when measured by a 1% by weight aqueous solution of the composition is 4 or higher comprising
   (a) blending 0.1–40% of an anhydrous base salt with 1–70% wetcake glyphosate to form a blended mixture I,
   (b) blending the following ingredients
      (1) 0–10% Of an anti-caking agent,
      (2) 0–1% of an anti-foaming agent,
      (3) 0.1–20% of a stabilizer selected from sodium metasilicate and sodium carbonate,
      (4) 0.1–40% of a sulfonylurea herbicide to form blended mixture II,
   (c) milling blended mixture II to form a powder,
   (d) blending mixtures I and II with 5–30% of a heat activated binder,
   (e) heating to 60°–70° C., and
   (f) cooling to 50° C. or lower wherein all of the above percentages are by weight based on the composition.

2. The process of claim 1 wherein the sulfonylurea herbicide is 0.5–20%.

3. A free flowing, non-caking, low attrition agriculturally suitable glyphosate composition comprising in weight percent based on the total composition weight
   (1) 1–70% wetcake glyphosate,
   (2) 2–8% water,
   (3) 0.1–40% anhydrous base salt,
   (4) 0–10% anti-caking agent,
   (5) 0–1% anti-foaming agent,
   (6) 0.1–20% stabilizer selected from sodium metasilicate and sodium carbonate,
   (7) 5–30% heat activated binder, and
   (8) 0.1–40% sulfonylurea herbicide provided that the pH of a 1% aqueous solution of the composition is higher than or equal to 4.

4. The composition of claim 3 wherein the wetcake is 20–60%, the anhydrous base salt is 4–30%, the anti-caking agent is 0–5%, the stabilizer is 2–15%, the heat activated binder is 10–25% and the sulfonylurea herbicide is 0.5–20%.

5. The composition of claim 3 wherein the anhydrous base salt is a sodium salt.

6. The composition of claim 3 wherein the sulfonylurea herbicide is methyl 2-[[[[(4-methoxy-6-menthyl-1,3,5-triazin-2-yl) amino]carbonyl]amino]-sulfonyl]benzoate.

7. The composition of claim 3 wherein the sulfonylurea herbicide is methyl 2[[[[(4,6dimethyl-2-pyrimidinyl)amino]carbonyl]amino ]sulfonyl ]benzoate.

8. The composition of claim 3 wherein the sulfonylurea herbicide is nicosulfuron.

9. The composition of claim 4 wherein the sulfonylurea herbicide is selected from chlorsulfuron; chlorimuron ethyl; tribenuron methyl; bensulfuron methyl; methyl 2-[[[[(4,6-dimethoxy-2-pyrimidinyl)-amino]carbonyl]amino]sulfonyl] -6-(trifluoromethyl)-3pyridinecarboxylate; methyl 2-[[[[[4-ethoxy-6-(methylamino)- 1,3,5 -triazin -2 -yl ]amino ]carbonyl ]amino ]sulfonyl]benzoate; 2-(2-chloroethoxy)-N-[[(4-methoxy-6-methyl-1,3,5-triazin-2-yl ) amino]carbonyl ]benzenesulfonamide; ethyl 5-[[[[(4,6-dimethoxy-2-pyrimidinyl) amino]-carbonyl]amino]sulfonyl]-1-methyl-1H-pyrazole-4-carboxylate; N-[[(4,6-dimethoxy-2-[pyrimidinylamino]-carbonyl]- 3-(ethylsulfonyl)-2-pyridinesulfonamide; N-[[(4,6-dimethoxy-2-pyrimidinyl)amino]carbonyl]-l-methyl- 4-(2-methyl-2H-tetrazol-5-yl)-1H-pyrazole-5sulfonamide; and methyl 2-[[[[ [4-(dimethylamino)-6-(2,2,2-trifluoroethoxy)-1,3,5-triazin-2-yl]amino]-carbonyl]amino]sulfonyl]-3-methylbenzoate.

* * * * *